United States Patent [19]

York

[11] 4,116,926
[45] Sep. 26, 1978

[54] STABILIZER FOR POLYMERS

[75] Inventor: James F. York, Morgantown, W. Va.

[73] Assignee: Borg-Warner Corporation, Chicago, Ill.

[21] Appl. No.: 853,923

[22] Filed: Nov. 22, 1977

Related U.S. Application Data

[63] Continuation of Ser. No. 603,848, Aug. 11, 1975, abandoned.

[51] Int. Cl.$^2$ .............................................. C08K 5/52
[52] U.S. Cl. ................................ 260/45.7 P; 260/967
[58] Field of Search ............................ 260/45.7 P, 967

[56] References Cited

U.S. PATENT DOCUMENTS

| | | | |
|---|---|---|---|
| 2,114,866 | 4/1938 | Vaughn | 260/25 |
| 3,553,298 | 1/1971 | Hodan | 260/950 |
| 3,787,537 | 1/1974 | De Marcq | 260/977 |

Primary Examiner—Eugene C. Rzucidlo
Attorney, Agent, or Firm—Joseph Shekleton

[57] ABSTRACT

An improved phosphite stabilizer for polymers, especially vinyl chloride polymers and olefin polymers. The phosphite is either a dialkylpentaerythritol diphosphite or a polyalkyl bisphenol-A polyphosphite; the improvement comprises the presence in such phosphite composition of a small proportion of triisopropanolamine.

15 Claims, No Drawings

STABILIZER FOR POLYMERS

This is a continuation, of application Ser. No. 603,848 filed Aug. 11, 1975, now abandoned.

BACKGROUND OF THE INVENTION

The purpose of stabilizers for polymers is to prevent deterioration of the polymers during processing at high temperatures, and also to permit manufacture of products with increased intrinsic quality because of the enhancement of their resistance to thermal and light degradation during use. In addition, because of the ability of these products to withstand more rigorous conditions, their versatility is increased and new areas of application are thereby opened.

An important class of polymer stabilizers are the organic phosphites. They include, as two especially useful groups, the dialkylpentaerythritol diphosphites and the polyalkyl bisphenol-A-polyphosphites. They are used widely in the stabilization of vinyl chloride polymers, polyolefins and styrene polymers such as ABS. The dialkylpentaerythritol diphosphites have the structural formula:

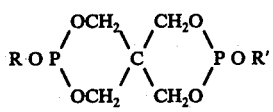

where R and R' are alkyl groups. The polyalkyl bisphenol-A polyphosphites have the structural formula:

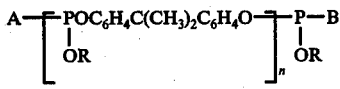

where A and B are each $HOC_6H_4C(CH_3)_2C_6H_4O$ or RO. R is alkyl and $n$ is 1–5.

Despite such wide usage, however, these types of stabilizers have not been entirely satisfactory, because of their own slight instability on storage. They tend to absorb moisture from a moist environment and their effectiveness as stabilizers for polymers seems to decline in direct proportion to the amount of water absorbed.

This disadvantage can be avoided by taking care to store and transport the stabilizer only in a dry atmosphere. Once incorporated in a vinyl polymer composition, no problem is presented apparently because of the essentially anhydrous condition of such polymer compositions.

Obviously, though, elimination or at least amelioration of the problem is desirable. A moisture-insensitive phosphite stabilizer will preclude the many inconveniences and expense associated with having to maintain an anhydrous environment.

U.S. Pat. No. 3,553,298 (Hodan) shows the stabilization of phosphite esters broadly by using any of several classes of amines including triisopropanol amine. See column 2, line 24 and Examples I–VI.

M. C. Imaev, Zhurnal Obshchei Khim. 31, 1767–70 (1961) shows the stabilization of lower trialkyl phosphites with organic and inorganic bases. The organic bases shown include pyridine, triethyl amine and dimethyl aniline.

U.S. Pat. No. 2,114,866 (Vaughn) shows the stabilization of esters of inorganic esters with an amine. While Vaughn is interested primarily in organic silicates he does mention also (see page 2, column 2, lines 17–22) borates, phosphates, "symmetrical" phosphites, arsenates and symmetrical arsenites.

U.S. Pat. No. 3,787,537 (Marcq) discloses a class of phosphite esters which are said to be stable to hydrolysis. Marcq refers also (see column 2, lines 9–10) to the stabilization of previously known phosphites by "a small quantity of a heavy amine, usually triisopropanolamine (French Pat. No. 1,582,387)". The cited French patent is a counterpart of the above Hodan et al U.S. patent.

None of the above disclosures, however, deal with the type of specific phosphites which are rendered resistant to hydrolysis by the invention.

SUMMARY OF THE INVENTION

Accordingly, the present invention is directed to the stabilization of a dialkylpentaerythritol diphosphite or a polyalkyl bisphenol-A polyphosphite wherein the alkyl groups each contain 8–20 carbon atoms, with a minor proportion of triisopropanol amine, and to polymer compositions containing the thus stabilized phosphites.

The Dialkylpentaerythritol Diphosphites

The dialkylpentaerythritol diphosphites above are disclosed in U.S. Pat. No. 2,961,454 where it is taught that such compounds may be prepared conveniently by reacting tri-2-chloropropyl phosphite with pentaerythritol to form the bis (2-chloropropoxy) spiro 1,3,2-phosphorinane

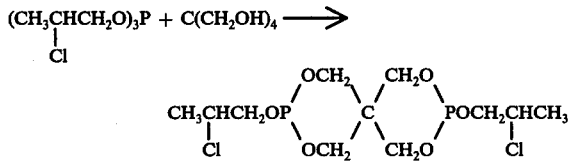

which then is reacted in turn with stearyl alcohol, for example, to form the desired distearyl pentaerythritol diphosphite.

Another method of preparation of these diphosphites is shown in U.S. Pat. No. 3,205,250; in that method triphenyl phosphite is used as the starting material instead of the tris-2-chloropropyl phosphite; this in turn requires the use of an alkaline catalyst.

The method of preparation seems to be unrelated to the moisture-sensitivity of the diphosphite, although the latter method is preferred, largely because of the lower cost of the triphenyl phosphite.

As indicated, the alkyl groups of the dialkylpentaerythritol diphosphite should contain from about 8 to about 20 carbon atoms. Typical diphosphites are those in which the alkyl groups are octyl, decyl, dodecyl, tetradecyl, hexadecyl, octadecyl and eicosyl. Both branched chain and straight chain alkyl groups are contemplated. Mixed alkyls such as are available from hydrogenated fatty esters, e.g., coconut oil, are suitable. Octadecyl (stearyl) is preferred because of the relative effectiveness and stability of the distearylpentaerythritol diphosphite which contains this group.

Where the alkyl groups are of higher molecular weight, i.e., 14–20 carbon atoms, the dialkylpentaerythritol diphosphite is a solid. Such solid materials are preferred stabilizers and their enhanced hydrolytic stability in accordance with the invention herein is especially surprising.

The additional presence of a small proportion of a higher alcohol, i.e., one having 14-20 carbon atoms, usually the same alcohol as that from which the above alkyl groups are derived, affects the physical character of the composition herein such that it is said to be "friable"; it is a freeflowing powder instead of a waxy material. This is desirable because it facilitates the handling of the composition. This friable result is accomplished by incorporating 5-10%, based on the weight of the composition, of the higher alcohol into the dialkylpentaerythritol diphosphite. This is done, most conveniently, by using a stoichiometrically excessive amount of the higher alcohol reactant in the preparation of the dialkylpentaerythritol diphosphite, so that the product mixture contains 5-10% of unreacted alcohol.

The Polyalkyl Bisphenol-A Polyphosphites

The polyalkyl bisphenol-A polyphosphites are disclosed in U.S. Pat. Nos. 3,356,770 (Larrison) and 3,662,032 (Kauder et al). They are prepared by the reaction of triphenyl phosphite, bisphenol-A and an alcohol of from about 8 to about 20 carbon atoms. Ordinarily, a catalyst is used; it may be an inorganic alkaline compound such as sodium or potassium hydroxide or carbonate; or it may be a diaryl phosphite such as diphenyl phosphite. The reaction may be carried out simply by mixing the three reactants, with or without a catalyst, and heating the mixture to drive off phenol until the desired product is obtained.

Alternatively, the triphenyl phosphite and bisphenol-A may first be reacted to give an intermediate product such as that described in U.S. Pat. No. 3,484,506 (Barananckas et al) and then this intermediate product reacted with the alcohol to give the final desired product.

Still another method of preparation involves the use of a trialkyl phosphite in place of the triphenyl phosphite and alcohol. Thus, the trialkyl phosphite is reacted with bisphenol-A in such proportions as to produce the desired polyalkyl bisphenol-A polyphosphite.

In all of these reactions the phenolic group of the bisphenol-A reacts with a phenyl or alkyl group of the triphenyl phosphite or trialkyl phosphite.

Other triaryl, trialkyl or trialkaryl phosphites may be used in place of the triphenyl phosphite although the reaction of bisphenol-A occurs most readily with the triaryl phosphites. It is quite obvious that structure of the final product will be determined largely by the relative proportions of reactants employed in its preparation. The identities of A and B in the above structural formula, in particular, will depend on the relative proportions of bisphenol-A and alcohol that are used. The value of $n$ will be governed to a large extent by the length of time the reaction mixture is heated, i.e., how much phenol is distilled from the reaction mixture (where triphenyl phosphite is the phosphite reactant).

The alkyl groups in the polyalkyl bisphenol-A polyphosphite are those which contain from about 8 to about 20 carbon atoms. A particularly preferred such material is one wherein these alkyl groups are derived from an alcohol mixture in which the alcohols each contain 12-15 carbon atoms.

DESCRIPTION OF THE SPECIFIC EMBODIMENTS

The stability of the compositions herein is shown by the results of tests carried out under conditions of controlled humidity and temperature. Five-gram samples of a distearyl pentaerythritol diphosphite, with and without varying proportions of triisopropanolamine, are weighed carefully, then placed in a humidity cabinet wherein the relative humidity and temperature are maintained at 32% and 25° C., respectively. The sample is weighed daily and the percentage increase (owing to water absorption) recorded. The results are shown in TABLE I.

TABLE I

| Time (Hrs.) | Triisopropanolamine | | | |
| --- | --- | --- | --- | --- |
| | 0 | 0.1% | 0.5% | 2.5% |
| 0 | 0 | 0 | 0 | 0 |
| 48 | 1.4 | 0 | 0 | 0 |
| 72 | 3.8 | 0 | 0 | 0 |
| 96 | 7.6 | 0.2 | 0 | 0 |
| 168 | 11.4 | 1.2 | 0 | 0 |
| 192 | 11.8 | 2.7 | 0 | 0 |
| 216 | 12.0 | 6.4 | 0.2 | 0 |
| 240 | 12.0 | 9.2 | 0.2 | 0 |
| 264 | 12.0 | 10.0 | 0.2 | 0 |
| 360 | 12.4 | 12.2 | 6.4 | 0 |
| 384 | 12.0 | 12.0 | 9.1 | 0 |

The distearylpentaerythritol diphosphite employed in the above tests contained 6% by weight of stearyl alcohol.

The increased hydrolytic stability of a polyalkyl bisphenol-A polyphosphite which contains a small proportion of triisopropanolamine is shown by the following data obtained from a similar test except that the relative humidity and temperature are maintained at 72% and 28° C., respectively. The results are shown in TABLE II.

TABLE II

| Time (Hrs.) | Triisopropanolamine | |
| --- | --- | --- |
| | None | 0.5% |
| 2 | 0 | 0 |
| 4 | 0 | 0 |
| 6 | 0.1 | 0.1 |
| 11 | 0.6 | 0.2 |
| 24 | 0.9 | 0.5 |
| 32 | 1.3 | 0.64 |
| 48 | 1.9 | 0.85 |

The polyalkyl bisphenol-A polyphosphite is prepared by mixing 1.0 mol of triphenyl phosphite, 0.5 mol of bisphenol-A, 2.0 mols of a mixture of alcohols each containing 12-15 carbon atoms, and a catalytic amount of sodium methylate, then heating the mixture to distill away phenol until no more would distill.

It will be noted that absorption of moisture in each case is significantly diminished by the presence of the triisopropanolamine. Such absorption of moisture is a direct reflection of hydrolysis of the phosphite stabilizer which in turn diminishes the effectiveness of the phosphite as a stabilizer.

The triisopropanolamine should be present in a concentration within the range of from about 0.01% to about 5% based on the weight of the stabilizer composition. Preferably, the concentration should be within the range of from about 0.1% to about 3.0%.

The effectiveness of the triisopropanolamine stabilized phosphites as stabilizers of vinyl polymers is shown by the test results set out in TABLE III. Those results are color ratings of formulated samples which have been processed at 180° C. on a two-roll mill. Samples are subjected to such processing treatment immediately after formulation and seven days after formulation; also, samples are removed from the mill and rated for color at 3-minute intervals.

The color rating is based on a scale of 0-10, where 0 is a very light yellow and 10 is a dark orange. In each case the test sample consisted of 100 parts of polyvinyl chloride, 12 parts of a copolymer of methyl methacrylate and styrene grafted onto an SBR substrate (impact modifier resin), 0.4 part of calcium stearate, 0.2 part of zinc octoate, 3.0 parts of epoxidized soybean oil, 0.4 part of a waxy ester of ethylene glycol and a $C_{32}$ fatty acid, 1.0 part of polymethylmethacrylate, 0.5 part of glycerol monostearate and 0.53 part or 1.0 part, as the case may be, of the triisopropanolamine stabilizer.

TABLE III

| Stabilizer Parts | DSPDP* | | | | DSPDP + TIPA** | | | |
|---|---|---|---|---|---|---|---|---|
| Blend Age | 0.53 | | 1.00 | | 0.53 | | 1.00 | |
| (days) | 0 | 7 | 0 | 7 | 0 | 7 | 0 | 7 |
| Flux | 1 | | 1 | 1 | 1 | 1 | 1 | 1 |
| 3 min. | 2 | | 2 | 3 | 2 | 2 | 2 | 2 |
| 6 min. | 2 | | 3 | 5 | 2 | 2 | 2 | 2 |
| 9 min. | 2 | | 3 | 5 | 2 | 2 | 2 | 2 |
| 12 min. | 2 | | 4 | 5 | 2 | 2 | 2 | 3 |
| 15 min. | 2 | | 5 | 5 | 2 | 3 | 2 | 3 |
| 18 min. | 2 | | 5 | 6 | 2 | 4 | 2 | 4 |
| 21 min. | 3 | | 5 | 7 | 3 | 5 | 2 | 4 |
| 24 min. | F*** | | 6 | 7 | 3 | 5 | 3 | 5 |
| 27 min. | | | 6 | F | F | 6 | F | 6 |
| 30 min. | | | F | | | F | | 6 |
| 33 min. | | | | | | | | 7 |
| 36 min. | | | | | | | | 8 |
| 39 min. | | | | | | | | F |

*Distearyl pentaerythritol diphosphite
**1.0% Triisopropanolamine
***Failure, i.e., suddenly turned black The stabilized phosphites herein are used in polymers in concentrations ranging from about 0.5% to about 3.0% based on the entire composition. They are especially useful in vinyl chloride polymers.

All parts and percentages herein are by weight unless otherwise expressly stated.

I claim:

1. An improved acidic composition comprising in combination a dialkyl pentaerythritol diphosphite or a polyalkyl p,p'-isopropylidene diphenol polyphosphite wherein the alkyl groups each contain 8-20 carbon atoms, and a minor proportion of triisopropanolamine.

2. The improved composition of claim 1 wherein the phosphite component is a dialkyl pentaerythritol diphosphite.

3. The improved composition of claim 2 wherein the alkyl groups of the dialkyl pentaerythritol diphosphite each contain 18 carbon atoms.

4. The improved composition of claim 2 wherein the diisopropanolamine is present in an amount of from about 0.01% to about 5% based on the weight of dialkyl pentaerythritol diphosphite.

5. The improved composition of claim 2 wherein the triisopropanolamine is present in an amount from about 1.0% to about 3.0% based on the weight of dialkyl pentaerythritol diphosphite.

6. The improved composition of claim 2 wherein there is present also a minor proportion of an alcohol containing 8-20 carbon atoms.

7. The improved composition of claim 2 wherein there is present also a minor proportion of stearyl alcohol.

8. The improved composition of claim 1 wherein the phosphite component is a polyalkyl p,p'-isopropylidene diphenol polyphosphite.

9. The improved composition of claim 8 wherein the polyalkyl p,p'-isopropylidene diphenol polyphosphite has the structure:

$$A \!-\!\!\left[\!\!\begin{array}{c} \text{P}-\text{OC}_6\text{H}_4\text{C}(\text{CH}_3)_2\text{C}_6\text{H}_4\text{O} \\ | \\ \text{OR} \end{array}\!\!\right]_n\!\!\!-\!\!\begin{array}{c} \text{P}-\text{B} \\ | \\ \text{OR} \end{array}$$

where A and B are each $HOC_6H_4C(CH_3)_2C_6H_4O$ or RO, P is alkyl of 8–20 carbon atoms, and n is 1–5.

10. The improved composition of claim 8 wherein the alkyl groups of the polyalkyl p,p'-isopropylidene diphenol polyphosphite each contain 12-15 carbon atoms.

11. The improved composition of claim 8 wherein the triisopropanolamine is present in an amount of from about 0.01% to about 5% based on the weight of polyalkyl p,p'-isopropylidene diphenol polyphosphite.

12. The improved composition of claim 8 wherein the triisopropanolamine is present in an amount of from about 1.0% to about 3.0% based on the weight of polyalkyl p,p'-isopropylidene diphenol polyphosphite.

13. The improved composition of claim 9 wherein n is 1.

14. The improved composition of claim 9 wherein A is RO and R is alkyl of 12-15 carbon atoms.

15. A vinyl polymer composition comprising a major proportion of a vinyl polymer and a minor proportion sufficient to stabilize said vinyl polymer of the improved phosphite composition of claim 1.

* * * * *